United States Patent
Doudoukjian et al.

(10) Patent No.: US 9,968,393 B2
(45) Date of Patent: May 15, 2018

(54) BENDING PIN

(71) Applicant: DePuy Synthes Products, LLC, Raynham, MA (US)

(72) Inventors: George Doudoukjian, West Chester, PA (US); Michael McGurk, West Chester, PA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 475 days.

(21) Appl. No.: 14/581,836

(22) Filed: Dec. 23, 2014

(65) Prior Publication Data

US 2016/0175020 A1 Jun. 23, 2016

(51) Int. Cl.
*A61B 17/88* (2006.01)
*A61B 17/80* (2006.01)
*A61B 17/17* (2006.01)

(52) U.S. Cl.
CPC ...... *A61B 17/8863* (2013.01); *A61B 17/1728* (2013.01); *A61B 17/8085* (2013.01); *A61B 17/8057* (2013.01)

(58) Field of Classification Search
CPC .................. A61B 17/8863; A61B 17/1728
See application file for complete search history.

(56) References Cited

U.S. PATENT DOCUMENTS

| | | | |
|---|---|---|---|
| 7,740,634 B2 | 6/2010 | Orbay et al. | |
| 7,771,433 B2 | 8/2010 | Orbay et al. | |
| 7,935,126 B2 | 5/2011 | Orbay et al. | |
| 8,172,886 B2 | 5/2012 | Castaneda et al. | |
| 8,241,338 B2 | 8/2012 | Castaneda et al. | |
| 8,337,533 B2 | 12/2012 | Raines et al. | |
| 8,419,745 B2 | 4/2013 | Sixto, Jr. et al. | |
| 8,545,540 B2 | 10/2013 | Castaneda et al. | |
| 8,568,462 B2 | 10/2013 | Sixto, Jr. et al. | |
| 8,603,147 B2 | 12/2013 | Sixto, Jr. et al. | |
| 8,834,537 B2 | 9/2014 | Castaneda et al. | |
| 8,858,562 B2 | 10/2014 | Orbay et al. | |
| 2004/0097950 A1 | 5/2004 | Foley et al. | |
| 2005/0234467 A1 | 10/2005 | Rains | |

(Continued)

FOREIGN PATENT DOCUMENTS

WO 2009/148762 12/2009

OTHER PUBLICATIONS

"New Product From AO Development" AOFoundation.org. https://www.aofoundation.org/Structure/innovation/tk-news/TK-System-Innovations-Magazine/Documents/TK_News_2004_1.pdf Davos Platz, Switzerland, 2004, 28 sheets.

*Primary Examiner* — David Bates
*Assistant Examiner* — Olivia C Chang
(74) *Attorney, Agent, or Firm* — Fay Kaplun & Marcin, LLP

(57) ABSTRACT

A system for bending an implant includes a drill guide extending longitudinally from a proximal end to a distal end, the drill guide including a distal portion having a first threading extending therealong to engage a threading along an interior of a bone fixation element receiving hole of an implant and a proximal portion having a second threading extending therealong and a bending pin extending longitudinally from a proximal end to a distal end including a recess extending proximally therefrom, the recess sized and shaped to receive the proximal portion of the drill guide and including a corresponding threading therealong for engaging the second threading.

15 Claims, 3 Drawing Sheets

(56) References Cited

U.S. PATENT DOCUMENTS

| | | | |
|---|---|---|---|
| 2006/0149250 A1* | 7/2006 | Castaneda | A61B 17/1728 606/86 B |
| 2007/0233111 A1 | 10/2007 | Orbay et al. | |
| 2007/0233112 A1 | 10/2007 | Orbay et al. | |
| 2008/0015591 A1* | 1/2008 | Castaneda | A61B 17/1728 606/86 A |
| 2009/0143825 A1 | 6/2009 | Graham et al. | |
| 2009/0228047 A1 | 9/2009 | Derouet et al. | |
| 2009/0318979 A1 | 12/2009 | Raines et al. | |
| 2009/0326590 A1 | 12/2009 | Foley et al. | |
| 2011/0166607 A1 | 7/2011 | Castaneda et al. | |
| 2011/0178522 A1 | 7/2011 | Orbay et al. | |
| 2011/0264100 A1 | 10/2011 | Sixto, Jr. et al. | |
| 2013/0006311 A1 | 1/2013 | Castaneda et al. | |
| 2013/0079829 A1* | 3/2013 | Globerman | A61B 17/7233 606/286 |
| 2013/0245699 A1* | 9/2013 | Orbay | A61B 17/8061 606/286 |
| 2014/0066943 A1 | 3/2014 | Sixto, Jr. et al. | |
| 2014/0172021 A1 | 6/2014 | Castaneda et al. | |
| 2014/0243828 A1* | 8/2014 | Heiney | A61B 17/8085 606/70 |
| 2015/0045804 A1 | 2/2015 | Orbay et al. | |
| 2015/0134011 A1* | 5/2015 | Medoff | A61B 17/1728 606/286 |
| 2015/0250485 A1* | 9/2015 | Niederberger | A61B 17/8057 606/281 |

* cited by examiner

BENDING PIN

BACKGROUND

Implants such as, for example, bone plates, must often be contoured to a fit a patient's specific anatomy to properly fix a fracture. The bone plates may be bent by a surgeon or other user using bending pins slid over drill guides that are pre-assembled with the bone fixation element receiving holes of the bone plate. Forces applied to the bending pins are transferred to the drill guides attached to the bone plate until the bone plate is bent, as desired. This process, however, exerts bending forces directly to the threading formed in bone fixation element receiving holes and, in some cases, may damage the bone plate beyond usability.

SUMMARY OF THE INVENTION

The present invention is directed to a system for bending an implant, comprising a drill guide extending longitudinally from a proximal end to a distal end, the drill guide including a distal portion having a first threading extending therealong to engage a threading along an interior of a bone fixation element receiving hole of an implant and a proximal portion having a second threading extending therealong and a bending pin extending longitudinally from a proximal end to a distal end including a recess extending proximally therefrom, the recess sized and shaped to receive the proximal portion of the drill guide and including a corresponding threading therealong for engaging the second threading.

BRIEF DESCRIPTION

DETAILED DESCRIPTION

Figure 1:
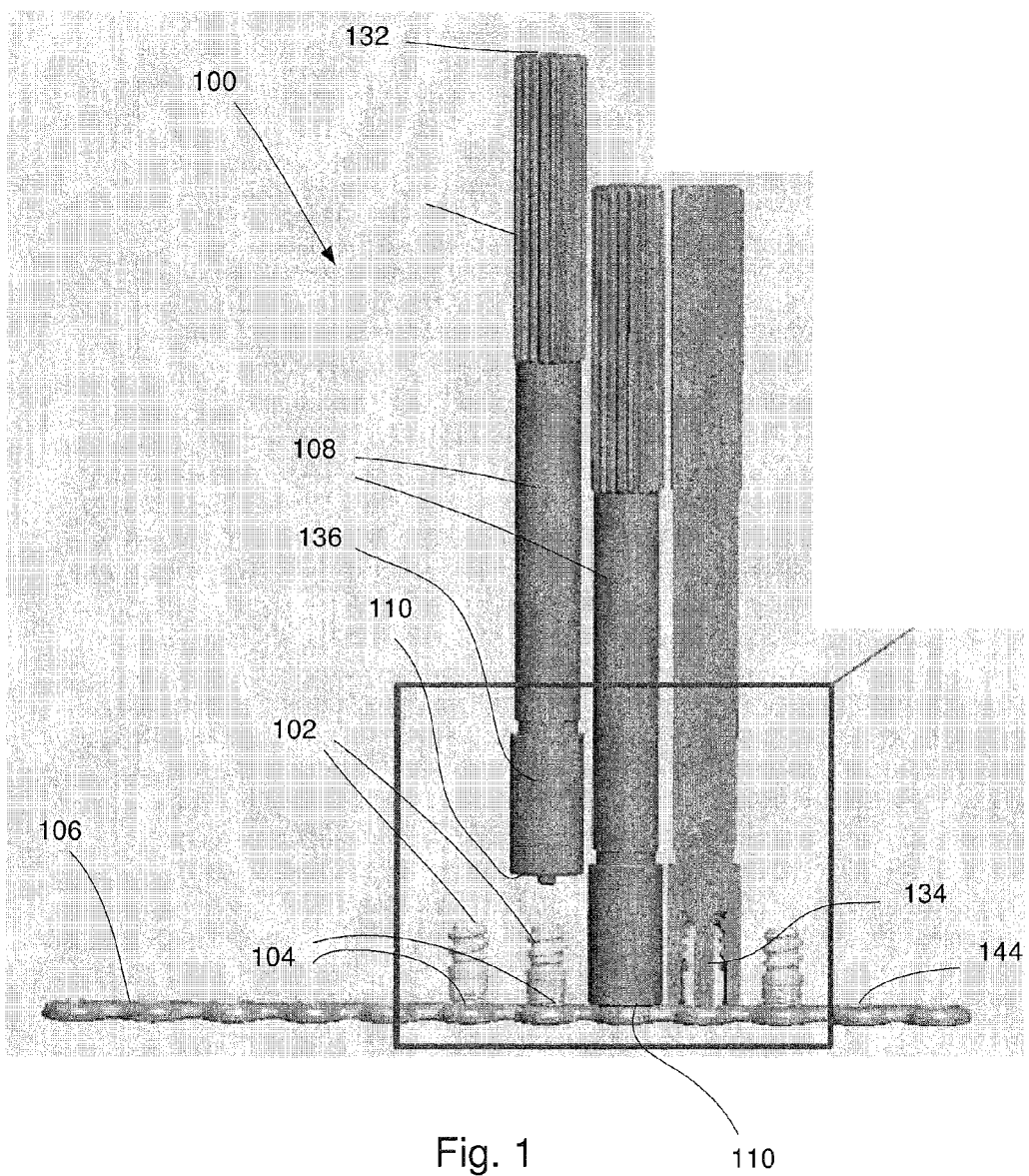
FIG. 1 shows longitudinal side view of a system according to an exemplary embodiment of the present invention.

The present invention may be further understood with referenced to the following description and the appended drawings, wherein like elements are referred to with the same reference numerals. The present invention is directed to a system for treating a bone and, in particular, to a system for bending an implant to correspond to a patient's anatomy. Exemplary embodiments of the present invention describe a system comprising a drill guide engaged within a bone fixation element receiving hole of an implant and a bending pin threadedly engagable with the drill guide to contact a surface of the implant so that bending forces applied to the bending pin are directly applied to the implant. It will be understood by those of skill in the art that the terms "proximal" and "distal" refer to a direction toward (proximal) and away from (distal) a user of the device.

As shown in FIGS. 1-5, a system 100 according to an exemplary embodiment of the present invention comprises a plurality of drill guides 102, each of which engages a bone fixation element receiving hole 104 of an implant such as, for example, a bone plate 106. The system 100 further comprises a plurality of bending pins 108, each bending pin 108 engagable with a corresponding one of the drill guides 102 so that a distal end 110 of the bending pin contacts the bone plate 106. Thus, when the bending pins 108 are moved relative to one another to bend the bone plate 106, the bending force is applied directly to a proximal surface 144 of the bone plate 106 (i.e., a surface which, when the plate 106 is mounted on a target portion of bone, faces away from the bone). Applying the bending forces to the proximal surface 144 of the plate 106 prevents damage to the bone fixation element receiving holes 104 of the bone plate 106. In contrast, conventional bending pins are slid over the drill guides, which are pre-assembled with the bone plate. Conventional bending pins and drill guides do not include any features that mate with one another so that, when bending forces are applied, one side of the bending pin will rise off of the plate, out of contact therewith, causing forces to be applied directly to the threads of the drill guide and the bone fixation element receiving holes of the bone plate with which the drill guides are engaged. This may cause the drill guides to back out of the bone fixation element receiving holes and/or cause extensive damage to the bone fixation element receiving holes of the bone plate. It will be understood by those of skill in the art, that the engagement of the bending pin 108 and the drill guide 102 of the present invention prevents damage to the threading of the bone fixation element receiving holes 104 of the bone plate 106 being bent thereby.

Figure 2:
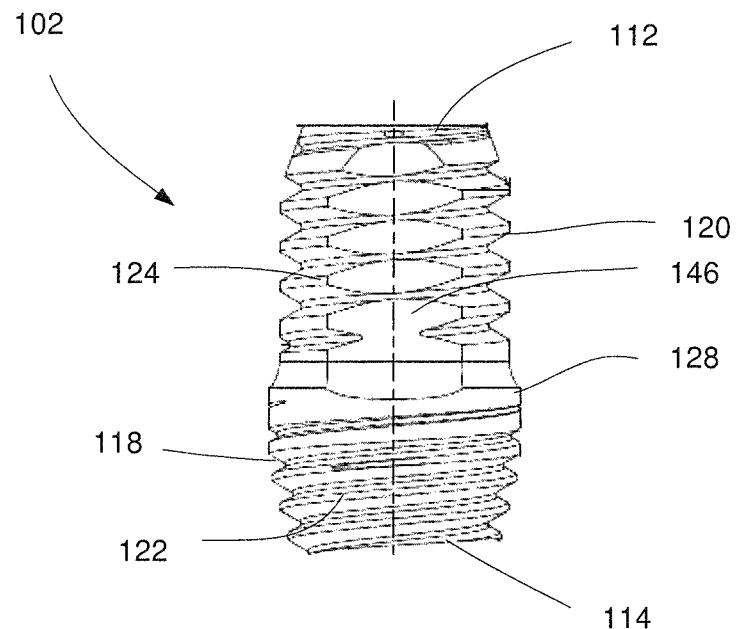
FIG. 2 shows a side view of a drill guide according to the system of FIG. 1.
Figure 3:
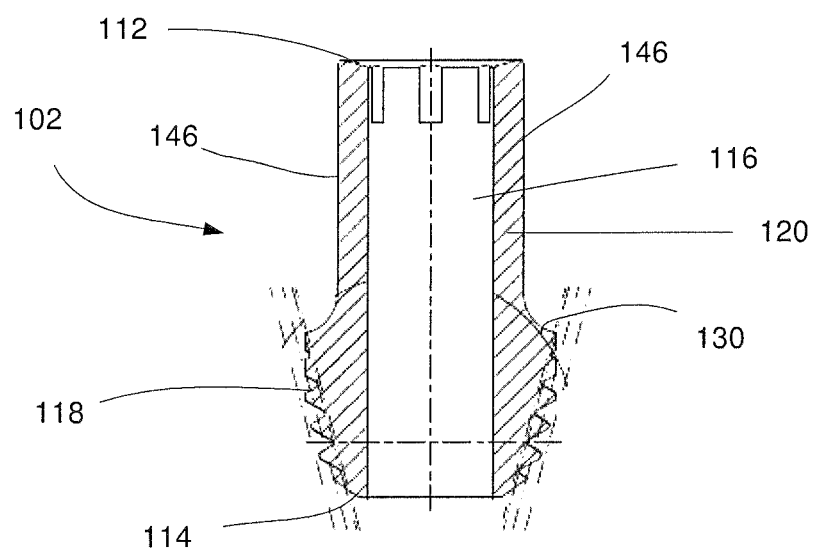
FIG. 3 shows a longitudinal cross-sectional view of the drill guide of FIG. 2.

As shown in FIGS. 2 and 3, each drill guide 102 extends longitudinally from a proximal end 112 to a distal end 114 and includes a channel 116 extending longitudinally therethrough to accommodate, for example, a drill bit for drilling a hole into a bone along an axis of the channel 116. The drill guide 102 include a distal portion 118 extending proximally from the distal end 114 for engaging a bone fixation element receiving hole 104 of the bone plate 106 and a proximal portion 120 extending distally from the proximal end 112 for engaging a corresponding one of the bending pins 108. The distal portion 118 includes a first threading 122 extending therealong for engaging a threading of the bone fixation element receiving hole 104. The proximal portion 120 includes a second threading 124 extending therealong for engaging a corresponding threading 126 of the bending pin 108. Extending between the distal portion 118 and the proximal portion 120, the drill guide 102 includes a non-threaded portion 128 that acts as a shoulder for directing force between the bending pin 108 and the drill guide 102. The first and second threadings 122, 124 may have different pitches.

In one exemplary embodiment, the distal portion 118 tapers from a proximal end 130 thereof toward the distal end 114 to engage a tapered bone fixation element receiving hole 104 (e.g., a locking screw hole). The proximal portion 120 may have a substantially constant cross-sectional area along a length thereof. The proximal portion 120 may also include a flat surface 146 extending along a length thereof. In an exemplary embodiment, the proximal portion 120 includes a pair of flat surfaces 146 diametrically opposed from one another. The flat surfaces 146 may engage a tool which is used to assemble the drill guide 102 with the bone plate 106 so that assembling the drill guide 102 to the bone plate 106 does not cause any damage to the second threading 124 of the drill guide 102 and/or any portion of the bending pin 108, which may otherwise be used to assemble the drill guide 102 to the bone plate 106.

Figure 4:
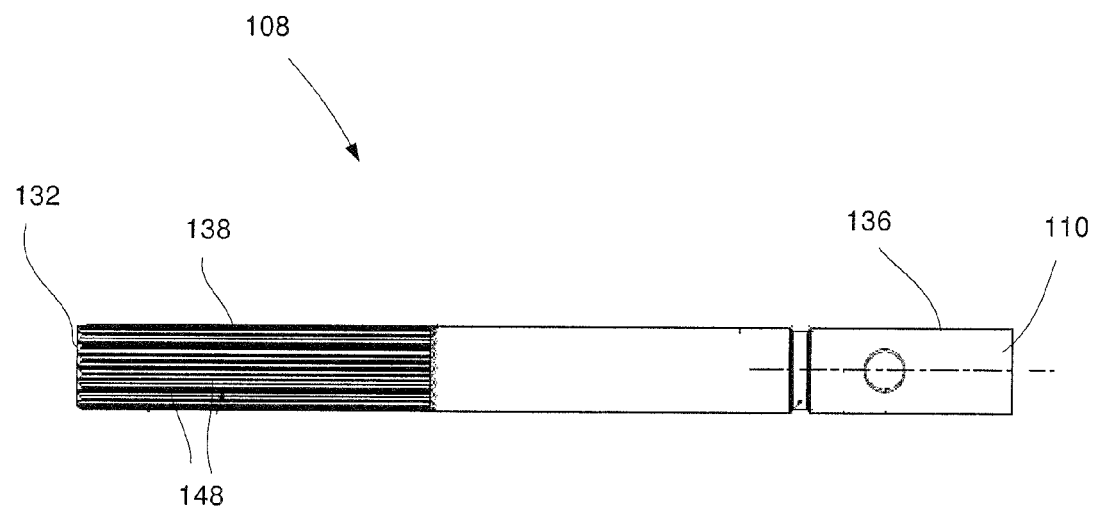
FIG. 4 shows a side view of a bending pin according to the system of FIG. 1.
Figure 5:
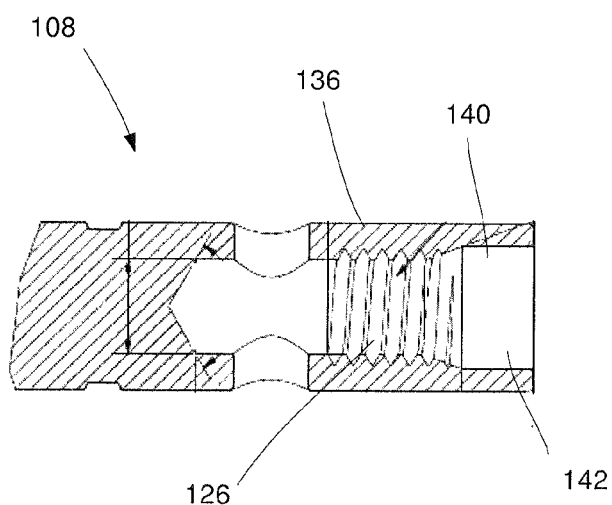
FIG. 5 shows a partial longitudinal cross-sectional view of the bending pin of FIG. 3.

As shown in FIGS. 4 and 5, each of the bending pins 108 extends longitudinally from a proximal end 132 to the distal end 110. The bending pin 108 includes a drill guide engaging portion 136 extending proximally from the distal end 110 and a gripping portion 138 at the proximal end 132 thereof. The gripping portion 138 according to this embodiment includes knurls 148 extending therealong and thereabout to facilitate a gripping thereof by a user. The drill guide engaging portion 136 includes a recess 140 at the distal end 110 sized and shaped to receive the proximal portion 120 of the drill guide 102. The recess 140 includes the threading 126 extending along a portion thereof for engaging the second threading 124 and a non-threaded portion 142 along a distal portion thereof for receiving the non-threaded portion 128 of the drill guide 102. The drill guide engaging portion 136 according to this embodiment also includes a pin 134 extending longitudinally within the recess 140 along a central axis thereof, as shown in FIG. 1. The pin 134, however, is not a required feature as the engagement between the proximal portion 120 of the drill guide 102 and the drill guide engaging portion 136 of the bending pin 108 is sufficient to transfer the bending force from the bending pin 108 to the proximal surface 144 of the drill guide 102. Each of the bending pins 108 may also include a throughhole 150 extending laterally through the drill engaging portion 136 so that the through-hole 150 is in communication with the recess 140. The through-hole 150 may be used to clean the recess 140, including the threading 126 and the non-threaded portion 142.

In use, the drill guides 102 may be pre-assembled with the bone plate 106 with the distal portion 118 of each of the drill guides 102 received within a corresponding one of the bone fixation element receiving holes 104 of the bone plate 106. In particular, the first threading 122 of the distal portion 118 is threadedly engaged with the bone fixation element receiving hole 104 so that the proximal portion 120 and the non-threaded portion 128 extend proximally from the proximal surface 144 of the bone plate 106. Each of the bending pins 108 is then engaged with a corresponding one of the drill guides 102. Specifically, the proximal portion 120 is received within the recess 140 of the bending pin 108, the bending pin 108 being rotated about a longitudinal axis thereof so that the threading 126 along the interior of the recess 140 engages the second threading 124. The bending pin 108 is rotated relative to the drill guide 102 until the distal end 110 contacts the proximal surface 144 of the bone plate 106 and the non-threaded portion 128 of the drill guide 102 is received within the non-threaded portion 142 at the distal end of the recess 140.

Once a desired number of bending pins 108 has been engaged with the drill guides 102, a user grips the gripping portions 138 of first and second ones of the bending pins 108, moving the first and second bending pins 108 relative to one another to bend the bone plate 106 as desired. As would be understood by those skilled in the art, different bending pins 108 may be moved relative to one another in selected directions to bend the bone plate 106 as desired. The non-threaded portion 128 of the drill guide 102 within the non-threaded portion 142 of the bending pin 108 acts as a guide to direct the bending force applied to the bending pin 108 to the drill guide 102. As described above, the contact between the bone plate 106 and the distal end 110 of the bending pin 108 applies the bending force directly to the proximal surface 144 of the bone plate 106, preventing damage to the bone fixation element receiving holes 104.

It will be apparent to those skilled in the art that variations can be made to the structure and methodology of the present invention, without departing from the scope of the invention. Thus, it is intended that the present invention cover the modifications and variations of this invention provided that they come within the scope of the appended claims and their equivalents.

What is claimed is:

1. A system for bending an implant, comprising:
    a drill guide extending longitudinally from a proximal end to a distal end, the drill guide including a distal portion having a first threading extending therealong to engage a threading along an interior of a bone fixation element receiving hole of the implant and a proximal portion having a second threading extending therealong; and
    a bending pin extending longitudinally from a proximal end to a distal end including a recess extending proximally from the distal end, the recess sized and shaped to receive the proximal portion of the drill guide and including a corresponding threading therealong for engaging the second threading,
    wherein, when the second threading and the corresponding threading engage one another, the distal end of the bending pin contacts a proximal surface of the implant.

2. The system of claim 1, wherein the drill guide includes a non-threaded portion extending between the proximal and distal portions.

3. The system of claim 2, wherein the recess of the bending pin includes a non-threaded portion at the distal end thereof for engaging the non-threaded portion of the drill guide.

4. The system of claim 1, wherein the distal portion of the drill tapers toward the distal end of the drill guide.

5. The system of claim 1, wherein a length of the recess and the corresponding threading is selected so that, when the drill guide is engaged to the implant and the bending pin, the distal end of the bending pin contacts a surface of the implant.

6. The system of claim 1, wherein the drill guide includes a channel extending longitudinally therethrough, the channel sized and shaped to accommodate a drill bit therein.

7. The system of claim 1, the bending pin including a gripping portion extending distally from the proximal end thereof, the gripping portion including knurls extending thereabout.

8. The system of claim 1, wherein the proximal portion of the drill guide includes a pair of flat surfaces extending along a length thereof, each of the pair of flat surfaces being diametrically opposed from one another.

9. A system for treating a bone, comprising:
    a bone plate including a plurality of bone fixation element receiving holes extending therethrough from a proximal surface which, when the bone plate is positioned along a bone, faces away from the bone, and a distal surface which, when the bone plate is positioned along the bone, faces toward the bone;
    a plurality of drill guides, each of the drill guides extending longitudinally from a proximal end to a distal end and including a distal portion threadedly engaged with a corresponding one of the bone fixation element receiving holes and a proximal portion extending proximally from the proximal surface of the bone plate, the proximal portion including a proximal threading extending therealong; and
    a plurality of bending pins, each of the bending pins extending longitudinally from a proximal end to a distal end including a longitudinal recess sized and shaped to receive the proximal portion of a corresponding one of the drill guides, the recess including a corresponding threading extending therealong to threadedly engage the proximal threading so that, when the proximal threading and the corresponding threading engage one another, the distal end of each bending pin contacts the proximal surface of the bone plate.

10. The system of claim 9, wherein each of the drill guides includes a non-threaded portion extending between the proximal and distal portions.

11. The system of claim 10, wherein the recess of each bending pin includes a non-threaded portion at the distal end thereof for engaging the non-threaded portion of the drill guide.

12. The system of claim 9, wherein the distal portion of each drill guide tapers toward the distal end thereof.

13. The system of claim 9, wherein each drill guide includes a channel extending longitudinally therethrough, the channel sized and shaped to accommodate a drill bit therein.

14. The system of claim 9, each bending pin including a gripping portion extending distally from the proximal end thereof, the gripping portion including knurls extending thereabout.

15. The system of claim 9, wherein the proximal portion of each drill guide includes a pair of flat surfaces extending along a length thereof, each of the pair of flat surfaces being diametrically opposed from one another.

* * * * *